Figure 1:
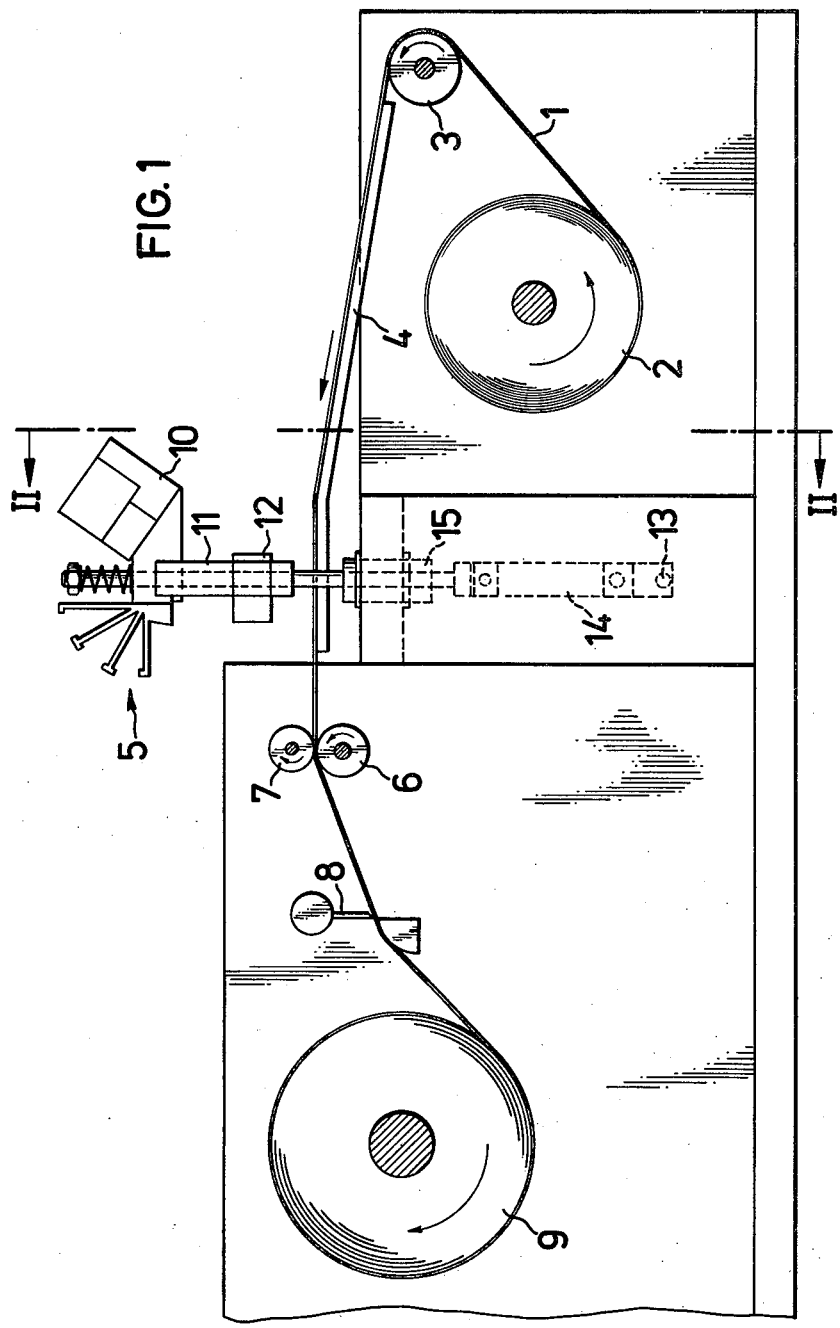

United States Patent [19]

Spitzer

[11] 4,453,406
[45] Jun. 12, 1984

[54] DEVICE FOR THE TRANSPORT OF TEST SPECIMENS IN STRIP FORM TO A MEASURING APPARATUS

[75] Inventor: Wolfgang Spitzer, Grünberg-Stockhausen, Fed. Rep. of Germany

[73] Assignee: Behringwerke Aktiengesellschaft, Marburg, Fed. Rep. of Germany

[21] Appl. No.: 331,544

[22] Filed: Dec. 16, 1981

[30] Foreign Application Priority Data

Dec. 18, 1980 [DE] Fed. Rep. of Germany ... 8033593[U]

[51] Int. Cl.³ .................. G01N 33/00; G01D 21/00
[52] U.S. Cl. .................. 73/432 R; 209/539; 198/456; 226/16; 422/66; 436/44
[58] Field of Search ............ 73/432 B, 432 Z, 432 R; 209/539, 540, 542, 545, 541; 198/345, 456; 226/15, 16; 422/66; 436/44

[56] References Cited

U.S. PATENT DOCUMENTS

| | | | |
|---|---|---|---|
| 3,300,114 | 1/1967 | Jacobsen | 222/16 X |
| 3,318,156 | 5/1967 | Dietert | 73/432 Z |
| 3,339,706 | 9/1967 | Arvidson | 198/456 X |
| 3,583,563 | 6/1971 | Muller | 209/545 |
| 3,621,972 | 11/1971 | Reuter | 198/456 |
| 3,776,700 | 12/1973 | Gallant | |
| 3,980,437 | 9/1976 | Kishimoto et al. | |
| 4,218,421 | 8/1980 | Mack, Jr. et al. | 422/66 |
| 4,279,514 | 7/1981 | Blümel et al. | 356/445 |
| 4,341,735 | 7/1982 | Seifried | 422/66 |

FOREIGN PATENT DOCUMENTS 2718193 1/1978 Fed. Rep. of Germany ...... 198/456
2014113 8/1979 United Kingdom .

Primary Examiner—S. Clement Swisher
Assistant Examiner—Tom Noland
Attorney, Agent, or Firm—Curtis, Morris & Safford

[57] ABSTRACT

Apparatus for the evaluation of test strips conveys the strips on a disposable web (e.g., a paper tape) from a first position where the test strips are placed onto the web, past a second position where the test strips are evaluated by a reflex photometer or other probe, to a take up position where the strips are wound up with the web for disposal. At the second position a barrier strip is disposed between two reciprocating arms or connecting rods, and serves to align the test strips with the probe. The connecting rods also carry at least one gripper having a beveled edge to urge the aligned test strip into registry with the probe. After evaluation, the barrier and gripper or grippers are lifted so that the evaluated test strip can be carried to the take up position.

10 Claims, 2 Drawing Figures

DEVICE FOR THE TRANSPORT OF TEST SPECIMENS IN STRIP FORM TO A MEASURING APPARATUS

This invention is directed to devices for evaluating test strips, e.g., urine test strips, and more particularly relates to devices in which test strips are transported to a predetermined position to be evaluated by means of a measuring probe.

In the art, devices have been proposed for passing test strips under a probe, using a drum carriage on which the strips are axially disposed. One such device is shown in U.S. Pat. No. 4,279,514. In that device test strips are placed in recesses on a drum parallel to the axis of the drum. The drum rotates forward to advance the strips from an insertion station to a testing station. A mobile probe at the testing station scans the length of the test strip at that station, and evaluates the test strip, for example, by reflex photometry. A disadvantage of the device of U.S. Pat. No. 4,279,514 occurs when placing the test strips, because these strips are normally somewhat bent. When determining maximum test strip throughput, the speed of operation is strictly limited by the incubation time required for the test strips.

In other previous test strip evaluation devices, test strips are placed lengthwise on a carriage and are passed in longitudinal direction under a probe. These devices have the disadvantage of needing great lengths of time for measurement, because of the necessary incubation time for the test strips. Thus, these devices are not well suited for serial testing.

Moreover, both types of previous devices have hygienic drawbacks: The elements of the devices which hold the test strips become contaminated and must be cleaned. Consequently, there is a risk of entraining the test liquid in the device and contaminating subsequent test strips with it.

Further, in the case of the second-mentioned devices, each of the test strips must be handled twice.

Accordingly, it is an object of this invention to provide an evaluation device for test strips which facilitates simple positioning of the test strips; which ensures precise adjustment of the strip positions under the measuring probe; and which prevents contamination of one test strip by another.

The above object is achieved by a device according to this invention, in which a belt, or belt-type conveyor for the test strips carries the strips from an insertion station to and beyond a testing probe. A crankshaft coupled by a connecting rod and to a barrier, which is disposed in the direction across the belt, serves to lower the barrier and at the same time lowers a beveled cant. The latter adjusts the lateral position of the test strips on the belt to register with the position of a test probe (which carries out the test strip evaluation, e.g., by reflex photometry). The speed of the belt can be adjustable to permit a predetermined time to pass, corresponding to the optimum test strip incubation time, between the dipping of the test strip in the test liquid (e.g., urine) and the passing of the test strip under the probe.

Preferably, the belt is a paper tape, or other disposable web, so that it can be disposed of after a one-time use. This aids in avoiding test strip contamination.

Figure 2:
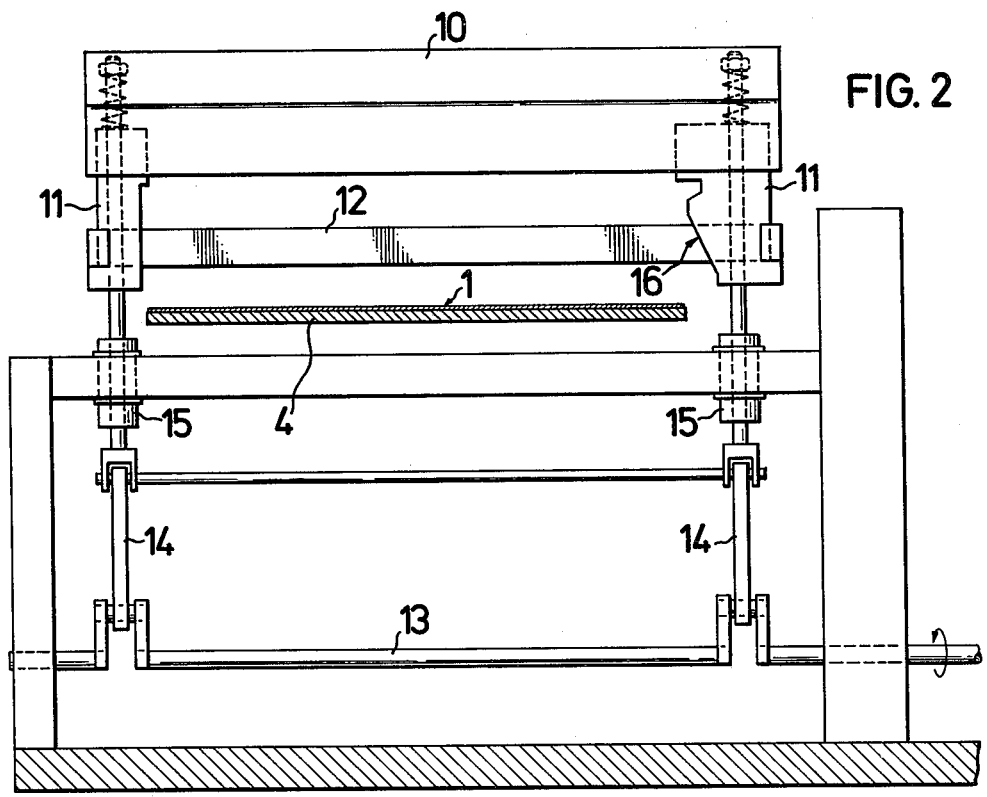

The above and many other desirable objects, features, and advantages of the invention will become apparent from the ensuing description of an illustrative embodiment, which is to be read in connection with the accompanying drawings, of which:

FIG. 1 is a side elevation of an embodiment of the evaluation device of this invention; and FIG. 2 is a sectional view along the plane II—II of FIG. 1.

With reference to the drawing Figures, the device of this embodiment of the invention is seen to comprise a housing for a paper web conveyor belt (1) mounted on a supply roll (2) in the housing. The belt (1) passes from the supply roll (2) over a guide roller (3) onto a support table (4), and then passes under the location of a probe or measuring device (5). From there, the belt passes between a drive roller (6) and a press roller (7), past a cutting device (8) to a take-up roll (9).

The measuring device (5), perhaps better shown in FIG. 2, includes a probe (10) carried by a pair of vertically-disposed grippers or claws (11) having at their lower ends projections on which a barrier strip or bar (12) is positioned and slidably mounted.

A crankshaft (13) is mounted in the housing parallel to the width direction of the paper belt (1). Crank arms of this crankshaft (13) are coupled to the grippers (11) by articulated connecting rods (14), which preferably pass through ball journals (15). The rotation of the crankshaft (13) thereby causes an up and down oscillation of the grippers (11), and hence causes lowering and raising of the barrier (12) to and from the belt (1), and also causes lifting and lowering of the probe (10).

A placing frame (not shown) is disposed on the paper conveyor belt (1) at a predetermined position on the table (4), and the belt (1) is drawn forward by the rollers (6) and (7), so that a test strip placed onto the belt (1) at the placing frame passes towards the position of the probe (10).

The measuring device (5) is lowered to such an extent that the barrier (12) and the belt (1) are slightly separated to define a slot therebetween, the height of which is smaller than the thickness of the test strip. The belt (1) conveys the test strip against the barrier (12) and continues its forward motion, at least for a predetermined distance, so that the test strip sits close to the barrier (12) and aligned parallel with it and with the probe (10).

Then, the probe (10) is lowered further onto the test strip by lowering the two grippers (11), and a beveled edge (16) or cant on one of the grippers (11) presses against an end of the test strip projecting over the corresponding edge of the belt (i.e., the right edge in FIG. 2).

This moves the test strip in its lengthwise direction (i.e., across the belt) to align or register test spots on the test strip with measuring channels on the probe (10).

The fact that the connecting rods (14) travel in the ball journals (15) ensures that the probe (10) is guided precisely into its measurement position. In such position the test strip is affixed by the force of the barrier (12) and the beveled edge (16) of the gripper (11), and the test portions of the test strip are measured, for example with respect to their reflection factors (i.e., by reflex photometry).

After the probe (10) finishes the measurement operation with respect to each test strip, the probe (10) and barrier (12) are lifted clear of the test strip. The belt (1) carries the test strip forward towards the take-up roll (9), where it is wound up together with the belt (1).

After completing a series of tests on a number of test strips, the material of the belt (1) can be cut using the cutting device (8), and the spent material removed from the take-up roll (9). This ensures an utmost degree of hygiene. The new end of the belt (1) resulting from the cut can be started anew on the take-up roll (9).

In the case of test strips used in clinical diagnosis, for example, a certain period of time (i.e., the incubation time) must pass between the wetting of the strip in the tested liquid and the measurement.

The device of this invention permits the operational speed to be varied so that the time that passes between placing of the test strip on the belt (1) and the measurement corresponds to the incubation time. Also, the operational speed can be varied for any particular incubation time by spreading the test strips more or less densely, as needed, over the conveyor belt (1).

The device can furthermore accomodate variations in operational speed, even though a uniform incubation time should be maintained throughout a series of test strips.

What is claimed is:

1. Apparatus for the evaluation of test strips comprising a housing; a conveying web for conveying the test strips, and extending from a supply of the web to a take up therefor, the web passing a first location at which the test strips are placed onto the conveying web and a second location at which the test strips are evaluated before the web passes forward to said take up; a probe mounted on said housing at said second location for evaluating each test strip passing thereunder; barrier means for aligning each test strip with the probe; cant means for displacing the test strip into registry with the probe; and reciprocating means for raising and lowering said barrier means and said cant means with respect to said housing while said web urges said test strip forward to effect the alignment and registry of the test strip; said reciprocating means including a pair of connecting rods journalled in said housing on opposite sides of said web; and said barrier means including a bar coupled to said connecting rods to move between a lowered position separated from said belt by less than the thickness of one of said test strips and a raised position in which said test strip can pass beyond said second location.

2. Apparatus for the evaluation of test strips as recited in claim 1, wherein said cant means includes at least one gripper mounted on one of said connecting rods, and having a beveled edge facing an edge of said web.

3. Apparatus for the evaluation of test strips as recited in claim 2, wherein said reciprocating means further includes crankshaft means for driving said connecting rods.

4. Apparatus for the evaluation of test strips as recited in claim 3, wherein said reciprocating means further includes ball journals in said housing journalling said connecting rods.

5. Apparatus for the evaluation of test strips as recited in claim 4, wherein said connecting rods are articulated.

6. Apparatus for the evaluation of test strips as recited in claim 1, wherein said web is a disposable tape.

7. Apparatus for the evaluation of test strips as recited in claim 6, wherein said supply includes a supply roll feeding out said disposable tape and said take up includes a take-up roll winding up said tape together with evaluated test strips; and further comprising a cutting device in said housing in advance of said take-up roll to cut said disposable tape to facilitate removal of the wound up tape and test strips following an evaluation procedure.

8. Apparatus for the evaluation of test strips as recited in claim 1, further comprising a table disposed on said housing beneath said web to support the same and extending at least from said first position to said second position.

9. Apparatus for the evaluation of test strips as recited in claim 1, further comprising a drive roller between said second position and said take up for advancing said web.

10. Apparatus for the evaluation of test strips as recited in claim 1, wherein said test strips are placed on said web with their lengthwise direction disposed transversely of said web.

* * * * *